United States Patent [19]

Rácz et al.

[11] Patent Number: 5,087,447

[45] Date of Patent: Feb. 11, 1992

[54] PHARMACEUTICAL PREPARATIONS OF HIGH GASTRIC ACID BINDING CAPACITY, DELAYED EFFECT AND OF INCREASED BIOAVAILABILITY

[76] Inventors: István Rácz, H-1105 Nebancsvirag 3; János Plachy, H-1025 Mandula 18; Péter Szentmiklost, H-1064 Rudas L 75, all of Budapest, Hungary

[21] Appl. No.: 420,280

[22] Filed: Oct. 12, 1989

Related U.S. Application Data

[62] Division of Ser. No. 165,102, Mar. 28, 1988, Pat. No. 4,921,707.

[30] Foreign Application Priority Data

Jun. 24, 1986 [HU] Hungary .............................. 2643/86
Apr. 21, 1987 [HU] Hungary .............................. 2643/86
Jun. 24, 1987 [WO] PCT Int'l Appl. ................. PCT/HU87/00026

[51] Int. Cl.$^5$ .................... A61K 31/78; A61K 33/08
[52] U.S. Cl. ................... 424/78.01; 424/690; 424/78.26; 424/78.17
[58] Field of Search .................... 424/78, 690, 81

[56] References Cited

U.S. PATENT DOCUMENTS 3,326,755 6/1967 Sheth .................................. 424/157

FOREIGN PATENT DOCUMENTS 0003589 8/1979 European Pat. Off. ............ 424/157

*Primary Examiner*—Frederick E. Waddell
*Assistant Examiner*—Zohreh Fay
*Attorney, Agent, or Firm*—Herbert Dubno; Jonathan Myers

[57] ABSTRACT

The invention relates to a new pharmaceutical preparation of high acid-binding capacity, of delayed effect, of increased bioavailability for neutralization of gastric acid and optionally to other pharmaceutical preparations acting in the gastrointestinal tract, first of all of laxative effect by mixing 100 parts by mass of a powdered basic magnesium compound or the powdered mixture of basic magnesium compounds and basic aluminium compounds with 2-2500 parts of a dry or swollen organic acid of polymeric character and therapeutically acceptable, e.g. cellulose-glycolic acid, starch-glycolic acid or polymer acrylic and/or methacrylic acid, letting this powdered mixture to stand for 1-24 hours at the temperature of 20°-80° C. after addition of 50-500 parts by mass of water and forming tablets or other pharmaceutical preparations, optionally after addition of 5-60 parts by mass of smoothing agents and/or other pharmaceutical excipients, or transforming the mixture containing the basic active ingredients and the polymeric organic acid in liquid suspension by adding water and optionally excipients.

4 Claims, 4 Drawing Sheets

PHARMACEUTICAL PREPARATIONS OF HIGH GASTRIC ACID BINDING CAPACITY, DELAYED EFFECT AND OF INCREASED BIOAVAILABILITY

This is a divisional of co-pending application Ser. No. 07/165,102 filed on Mar. 28, 1988 now U.S. Pat. No. 4,921,707.

The invention relates to the production of a new pharmaceutical preparation of high gastric acid binding capacity, of delayed effect and of high bioavailability and eventually to other pharmaceutical preparations acting in the gastrointestinal tract, for instance to laxative preparations of high swelling and water retaining capacity (the so called "bulk" laxative preparations).

The clinical experience of pharmacotherapy confirmed extensively in the last years that paralelly to the preparations reducing the gastric secretion by selective inhibition of the histamine-$H_2$-receptors, the classical gastric acid neutralizing preparations, the so called antacids play also actually an important role in the therapeutics of hyperacid conditions and gastric ulcers. This fact is explained, first of all, by the data demonstrating that the antacid preparations provoke much less side effects and, on the other hand, the well formulated and correctly dosed antacids meet with all the therapeutical demands and give reliable results. Therefore in this field of pharmaceutical investigations great efforts have been made in the last years for developing antacid preparations of high bioavailability.

The biovailability, the activity of antacid drugs, their action on the pH value of gastric juice and the course of their effect as a function of time may be characterized by the Rossett-Rice test (N. E. Rossett, M. L. Rice: Gastroenterology, 26. 940(1954)), as shown in FIG. 1. For the classical antacid preparations the mode of action and its course as function of time follow generally the Curve I.

It shows that after administration of the preparation the pH value of the hyperacid gastric juice rises only for a short time, but not only to the optimal value of 3-5, but to much higher ones. The area of activity below the Curve I is divided in two parts: the part $A_o$ corresponding to the optimal pH-range (3-5) and the area $A_{re}$, corresponding to higher pH-values. This latter antacid activity is worthless, even harmful for the organism, due to the supression of the pepsin activity and to the so called "rebound effect", provoking reactive hydrochloric acid secretion. The elimination of these disadvantages has been intended by the application of antacid preparation of controlled dissolution rate (sustained-release preparations). Their application does not cause an unnecessary, sudden, high pH rise of short duration but they maintain the pH value for a long time in the optimal pH range, assuring the full biological availability of the antacid activity of the preparations, as shown by the Curve II in FIG. 1.

Among the antacid preparations actually applied especially the non-systemic antacids prevail, id est, preparations containing active ingredients of basic character, whose cation is evacuated from the organism as a poorly soluble salt formed in the intestines and does not disturb the acid-base equilibrium, even in cases of long lasting administration. Such a cation is magnesium, which is transformed in the bowels into the scarcely soluble magnesium carbonate and is evacuated from the organism in this form.

Many attempts have been made in the last years for the development of the preparations of this type, especially for increasing the acid-binding capacity, the prolongation of the duration of their action, the improvement of the taste or for rendering more easy or comfortable the ingestion using pharmacotechnical methods. So, for instance, the U.S. Pat. No. 4,271,142 describes the mode of production of an antacid preparation of simple handling and pleasant taste, which may be transformed in suspension in situ before ingestion.

The U.S. Pat. No. 3,843,778 describes a notable new technical method. According to this invention the active antacid ingredient containing granules is provided with an oily coating of hydrocarbon type and these coated granules are used for the preparation of suspensions or tablets. The product so obtained is tasteless and may be flavored at discretion.

Various new proceedings have been proposed for increasing the duration of the action. For instance, the Swiss Patent Specification No. 621,063 discloses a preparation of delayed action, consisting of tablets of various layers, but the method there described is suitable, in the first place, for preparations, whose active ingredient content is not greater than 300 mg.

But in antacid preparations the amount of the active ingredient may reach and even pass over 800 mg and so this proceeding is not very suitable for the preparation of antacid tablets of delayed effect.

The inventors of the present invention disclosed in the Hungarian Patent Specification No. 167,604 a process for the production of tablets characterized by regulated dissolution rate of the active ingredients by using for the granulation of the powdered mixture containing the active ingredients and the excipients a special hydrophobic component (e.g. stearic acid) and as a hydrophilic component an emulsion containing two different emulgators of regulated HLB (hydrophilic-lipophilic balance) value.

The same authors, in the Hungarian Patent Specification No. 179,474 disclosed a process for obtaining solid pharmaceutical preparations of regulated active agent dissolution rate and increased duration of action, consisting of the addition of an amphoteric gel-forming substance to the powder containing the active ingredients and the excipients, e.g. dry, powdered tragacanth gum and/or carboxymethylcellulose, a fraction of this amphoteric gel-forming substance may be added to the mixture of the active ingredients and the excipients already before granulation. The granules of these preparations adhere to the gastric mural due to the effect of the amphoteric gel-forming substance and prolong the presence of antacid material in the stomach and so they exert a sustained-release action.

In the field of production of pharmaceutical preparations in the form of tablets a new technical process was developed by the invention of the so called "liquid wafer" type pharmaceutical tablets, which, when put into the oral cavity, disintegrate immediately, generally causing a cool sensation and provoking salivation. Consequently, the disintegrated tablet may be swollen easily, quickly and also without taking water. This fact is not only comfortable for the patients, but it renders also possible the ingestion of the drugs in any situation, for instance during travelling or in other conditions, where comfort is absent.

In the field of antacid tablets the method disclosed by Harden (British Patent Specification No. 1,601,833) may be succesfully adapted, this invention proposes in addition to aluminium and magnesium hydroxides as active ingredients the application of the sodium salt of an organic polymeric acid, which is especially active im promoting the disintegration (Primojel). The great swelling capacity of this substance plays an important role in obtaining the desired physical properties of the preparation.

For antacid preparations the delayed action is very desirable, but as far as here it has not been achieved with the "liquid wafer" preparations. No references are found in the literature about the simultaneous obtention of the "liquid wafer" character and the delayed action and generally, the "liquid wafer" character, expressing the postulate of rapid disintegration, is considered as incompatible with the different manipulations of embedding and coating and the pertinent application of slowly dissolving, hardly swelling excipients or greasy embedding matters.

The present invention is based on the recognition of the surprising fact, that the sustained-release acid binding action and the "liquid wafer" character may be achieved in the very same preparation by a single technical operation, by assuring a high acid-binding capacity for each dosing unit having the mass of a normal tablet. This aim is achieved according to the present invention by using as the active antacid ingredient a highly basic magnesium compound or a mixture of basic magnesium and aluminium compounds and by contacting the active ingredient in an aqueous medium with a weak organic acid of polymeric character. In this case the weak polymeric acid reacts with the basic metallic compound producing a substance of high swelling capacity, able to be formulated habitually as a preparation for oral administration, expediently as tablets. The product of high swelling capacity, incorporated into the preparation assures the rapid disintegration of the tablets after ingestion and hence, on the other hand, the "liquid wafer" character is present and on the other hand, when arriving into the stomach, the mass adheres to the gastric wall and reacts slowly with the gastric acid, a stronger one, than the polymeric acid component incorporated in the tablets, assuring a delayed acid-binding action of long term. It is evident, that the pH increasing due to $OH^-$ flow provided by the preparation because of the viscosity enhancing and therefore diffusion decreasing effect—may be controlled according to the wanted level.

An additional important advantage of the process described in the present invention consists of the fact, that by assuring at the same time the "liquid wafer" character and the high acid-binding capacity, the delayed action may be combined with a prompt incipient action. It may be achieved according to the invention by mixing the basic magnesium compound (respectively the mixture of basic magnesium and aluminium compounds) with an amount less than stoichiometrically correspondent to that of the weak acid of polymeric character and this powder mixture is submitted to the habitual wet granulation process. Under these conditions only a fraction of the active antacid ingredients/s/ reacts with the polymeric acid, the specific acid-binding capacity of the substance is reduced only partly. The product obtained by the reaction of a part of the antacid substance with the polymeric acid characterized by high swelling potency, is sufficient for assuring the sudden disintegration of the tablets and so far assuring the "liquid wafer" character. On the other hand, the non-reacted part of the antacid substance is suitable for rapid acid-binding. It means that when taking the tablet, that part of the antacid ingredient, which may be considered as a stoichiometrical excess, assures the prompt incipient acid-binding capacity, forming the "fast-releasing" fraction and the other part of the active antacid ingredient enters in reaction with the polymeric acid and supplies the slowly reacting fraction of the dose. This fraction reacts slowly with the stronger gastric hydrochloric acid, forming the "slowly-releasing" part of the active ingredient of the dose ingested in the very same preparation.

In the case of this especially advantageous variant of the execution of the process described in the present invention, "liquid wafer" type antacid preparations of high acid-binding capacity and of optimized bioavailability may be obtained by the simple and habitual process of granulation, which combines the prompt incipient action with a delayed one and the relation of the prompt initial and of the delayed actions may be varied between wide limits by changing the ratio of the active antacid ingredient and the weak polymeric acid.

It may be deduced from the exposed facts, that when the basic active antacid ingredient and the polymeric organic acid are used in stoichiometric amounts or the polymeric organic acid is present in excess as compared with the active antacid ingredient, all the basic antacid ingredient reacts with the polymeric organic acid and the pharmaceutical preparation contains the active antacid ingredient exclusively in this reacted form, only the delayed action will get across in the absence of the promptly acting component. Inversely, when polymeric organic acid (e.g. cellulose-glycolic acid) is applied in a very great excess (e.g. for 1 mass unity of magnesium oxide 30–50 mass unities), the so called "bulk" laxative action will prevail due to the high swelling and water-retaining capacity of this component. In this way, when proceeding according to the process described in the present invention, a "liquid wafer" type laxative preparation may be obtained, which acts by increasing the mass of faeces.

That means, that the invention refers to a process for the preparation of pharmaceutical preparations of high acid-binding capacity and delayed action, with increased bioavailability and eventually exerting also other actions developed in the gastrointestinal tract, e.g. laxative effect, characterized by mixing 100 parts by mass of a powdered basic magnesium compound or a powder consisting of a mixture of basic magnesium compounds and basic aluminium compounds with 2–2500 parts by mass of a therapeutically acceptable, in water swelling organic acid of polymeric character and this powder mixture is granulated with 50–500 parts by mass of water, optionally after addition of 5–50 parts by mass of a smoothing agent and/or other pharmaceutical excipients like colloidal silicic acid, polyvinyl-pyrrolidone, sodium saccharimide and/or other flavoring or perfuming agents and tablets or other solid pharmaceutical products are formulated or the basic active ingredient and the polymeric organic acid containing powder mixture is transformed in a suspension by addition of water, eventually after addition of the mentioned excipients.

In the process described in the invention as basic magnesium compounds, first of all, magnesium oxide, magnesium hydroxide or basic magnesium carbonate and as basic aluminium compound chiefly aluminium hydroxide may be used. As an in water swelling weak polymeric organic acid free carboxyl groups containing organic polymers may come in consideration, e.g. cellulose-glycolic acid (carboxymethylcellulose), starch-glycolic acid (carboxy-methyl-starch), carboxy-polymethylene (for instance the product known by its commercial name "Carbopol 940"), polymeric derivatives of acrylic and methacrylic acids, (especially the product "Eudragit L 100-55" used also as pharmaceutical excipient).

The weak organic acid of polymeric character is used, as mentioned above, in the following manner:
- a/ in the amount sufficient for the complete reaction with the basic substance, when exclusively the production of a preparation of retarded action is aimed,
- b/ in less amounts, when preparations of combined—prompt and retarded—effect are aimed, in ratios corresponding to the obtention of the desired action,
- c/ in a considerable excess, when a preparation of "bulk" laxative effect is wanted.

In each case, the most convenient amount may be determined by taking into consideration the number of the reactive basic groups of the basic compounds, as well as the number of the free reactive groups of the polymeric organic acid.

The action of the weak, water-swellable organic acids of polymeric character, manifesting itself in the delayed of the liberation of the active ingredient, id est, of the magnesium or aluminium compounds, respectively, is based according to the present invention of the fact, that the viscosity of these substances increases considerably as a result of the reaction of salt formation with the basic compounds. The salt of the polymeric organic acid, swollen in the presence of water, obtained as a result of its reaction with the basic substance, forms in the stomach a very adhesive mass of high viscosity, from which the gastric hydrochloric acid only slowly dissolves the basic active ingredient. This quality of the polymeric organic acids able to swell in water may be demonstrated also experimentally.

Figure 1:
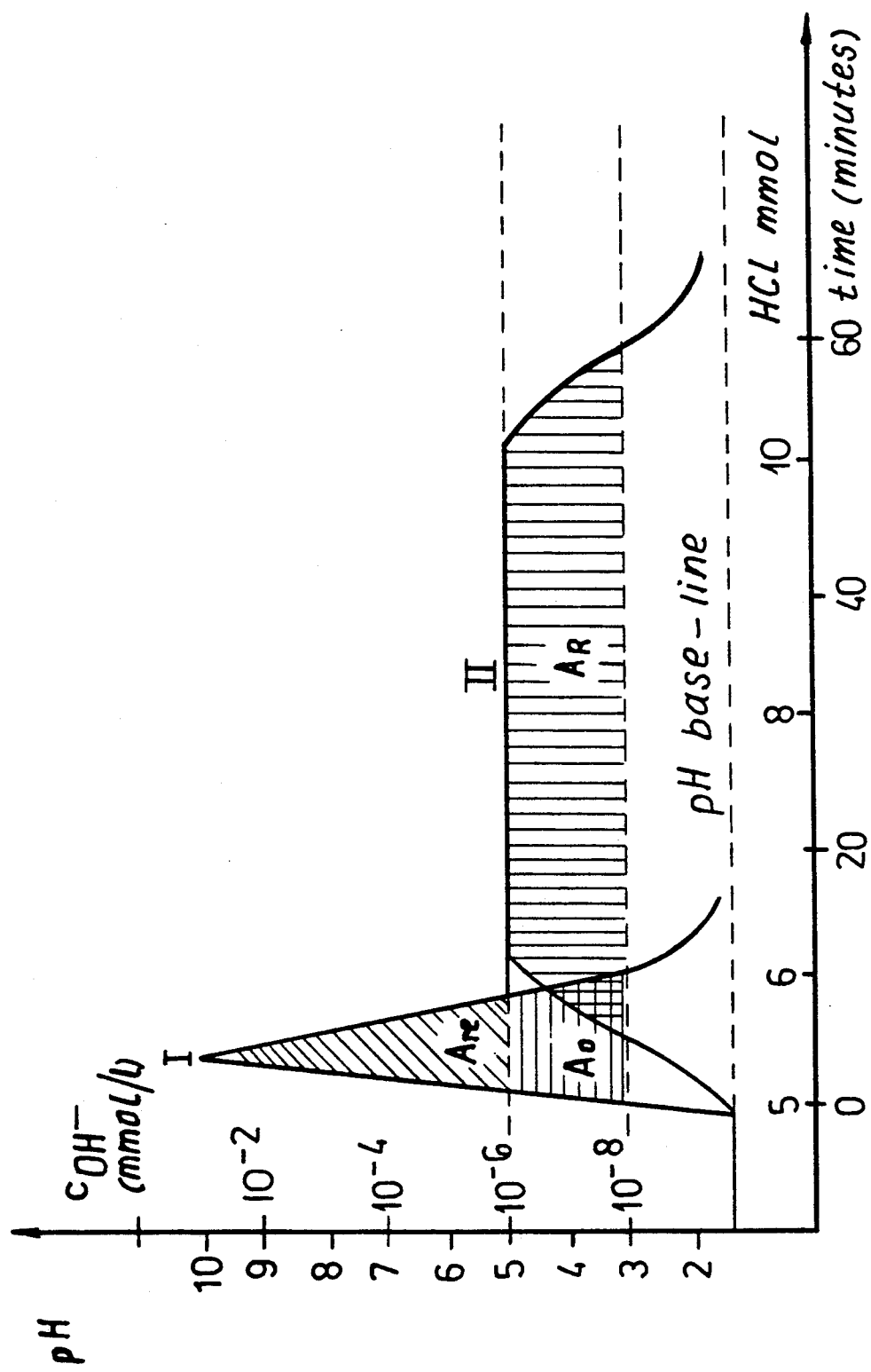
FIG. 1 is a graph showing bioavailability as a function of time for antacid preparations.
Figure 2:
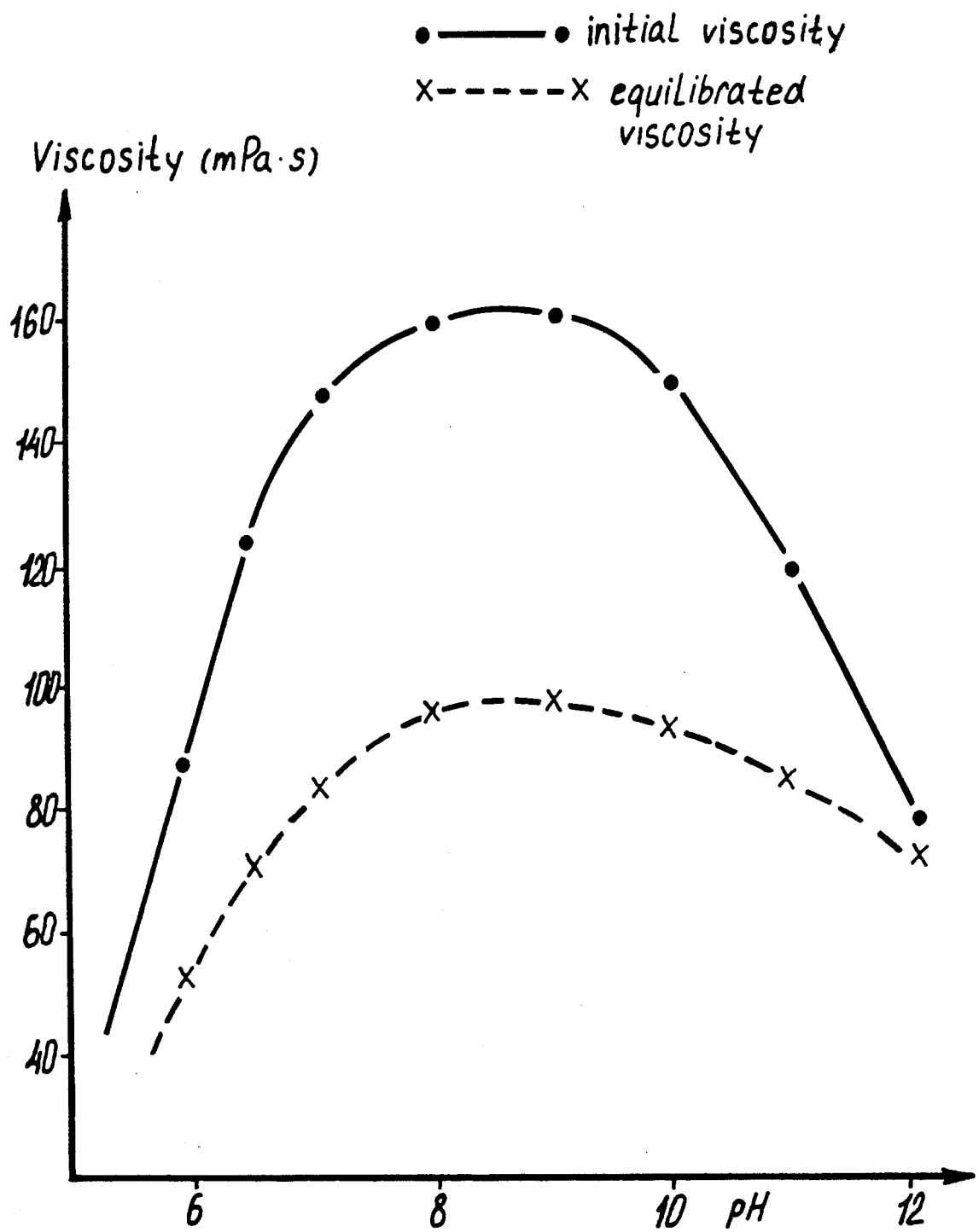
FIG. 2 is a graph of the pH dependency of viscosity.

FIG. 2 shows the dependance of the viscosity of an 1 percent aqueous dispersion of Eudragit L 100-55 on the pH-values. Evidently, the originally low viscosity of the acid dispersion is gradually increasing with salt formation in the presence of gradually increasing amounts of sodium hydroxide, at weakly basic pH-values the initial viscosity, as well as the equilibrated viscosity obtained by the destruction of the gel structure and controlled by repeated measurements reaches a maximum and then it is decreasing at very high pH-values (not viable under physiological conditions). The maximum of viscosity at weakly basic pH-values may be produced also by salt formation with basic magnesium compounds.

This property of the weak organic acids of polymeric character, swelling in water prevails also in the process described in the present invention: the adhesive polymer of increased viscosity increases the time of retention in the stomach of the basic antacid preparation as a result of the salt formation with magnesium and delays the liberation of the antacid active ingredient.

When the preparation is produced according to the present invention, the reaction of the basic compound with the swelling polymeric organic acid is carried out in the presence of water and some time is required for the completion of the reaction. Therefore it is advantageous to let the mixture of the basic substance and of the swelling polymeric organic acid stand for some time before granulation of the wet mass occurs and to let time enough for the swelling of the polymeric acid, as well as for its reaction with the basic compound.

This aim, the promotion of the reaction of the basic compound with the polymeric acid may be realized also by another advantageous mode of realization of the process: by letting the polymeric organic acid swell in water and by adding afterwards the basic compound to the swollen material. In dependence of the desired composition of the mixture an excess of the basic compounds and/or water may be added for obtaining the desired consistence, apt for granulation.

The dry granulated mass may be enriched eventually before compression of the tablets or its transformation in other solid preparations, by the addition of different excipients generally used in pharmaceutical practice, especially flavoring and/or perfuming agents, e.g. mannitol, xylitol and/or essential oils, agents promoting the disintegration of the tablets, e.g. cross-linked polyvinyl-pyrrolidone and similar compounds.

The preparations corresponding to the present invention may be produced also as liquid suspensions. In this case the mixture of the basic substance and of the polymeric acid is not granulated but transformed in suspension with an additional amount of water. This suspension—eventually after dilution with more water and addition of preservative agents, e.g. sodium benzoate—may be applied as an antacid preparation or elaborated to other physiologically useful products, e.g. to soft drinks with antacid effect.

The following examples illustrate suitable methods for the practical application of the present invention.

EXAMPLE I 500 g of magnesium oxide and 50 g of dry, powdered polymerized acrylic acid (Carbopol 940) are mixed, homogenized and sieved through a sieve with openings of 0.5 mm. 600 g of deionized water is added to the sieved powder. The wet mass is kneaded together and let stand for 24 hours at room temperature and then passed through a sieve with an opening of 2 mm. The granulated mass is dryed. 170 g of mannitol, 23.5 g of cross-linked polyvinyl-pyrrolidone (Polyplasdon XL), 2 g of hydrophobized colloidal silica acid (Aerosil R 972) and 1.5 g of sodium saccharimide are added to the mass. It is regranulated through a sieve with opening of 1.2 mm and using this mixture of 0.75 g individual mass is compressed.

Figure 3:
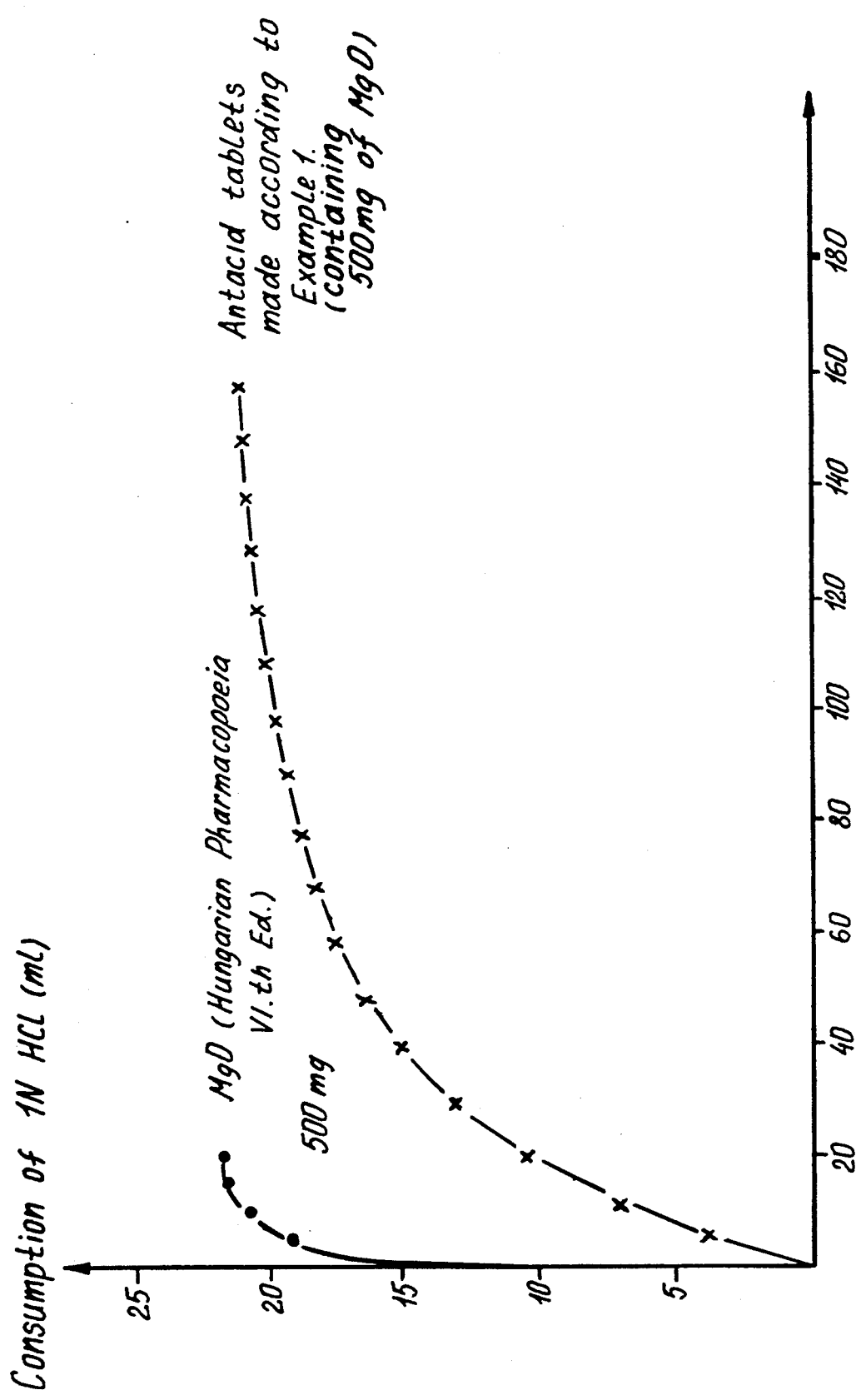
FIG. 3 is a graph of the duration of the action of the preparation of Example I.

The duration of the action of this antacid preparation so produced was compared with the action of magnesium oxide of the purity prescribed in the pharmacopoeia and the result presented in FIG. 3 was obtained. In acidic medium of constant pH 3.0 of 37° C. temperature, stirred at 300 rpm, magnesium oxide produces almost instantaneous neutralization, but the preparation made according to Example I, containing identical amounts of magnesium oxide does not finish the neutralization process even in 120 minutes.

EXAMPLE II 30 g of cellulose-glycolic acid (carboxymethyl-cellulose) prepared from sodium carboxymethyl-cellulose (corresponding to the prescriptions of the VIth Hungarian Pharmacopoeia by precipitation with alcohol containing 20 percent of the most concentrated hydrochloric acid) is allowed to swell in 100 g of deionized water at 40° C. for 2 hours, 500 g of magnesium oxide and 700 g more of water are added and a homogeneous mass is produced. Th wet mass is granulated and tablets are made as indicated in Example I.

EXAMPLE III

A mixture of 700 g of powdered magnesium carbonate and of 50 g of powdered polymerized methacrylic acid (Eudragit L 100 55) is wetted with 700 g of deionized water and a homogeneous mass is produced. The wet mass is treated as described in Example I and is granulated and the dry granulate is enriched with 200 g of mannitol, 42.5 g of crosslinked polyvinyl-pyrrolidone (Kollidon CL), 2.5 g of hydrophobized colloidal silica (Aerosil R 972), 2.5 g of sodium saccharimide and tablets of 1 g individual mass are compressed.

EXAMPLE IV 150 g of magnesium oxide and 50 g of polymerized acrylic-methacrylic acid (Eudragit L 100 55) are powdered and 800 g of deionized water are added to the dry mixture. It is allowed to stand for 2 hours with periodical stirring. Then 350 g of a mixture of magnesium hydroxide (aluminium hydroxide is added in the form of a dry gel and the wet mass so obtained is further processed as described in Example I for the production of tablets of 0.75 g individual mass.

Figure 4:
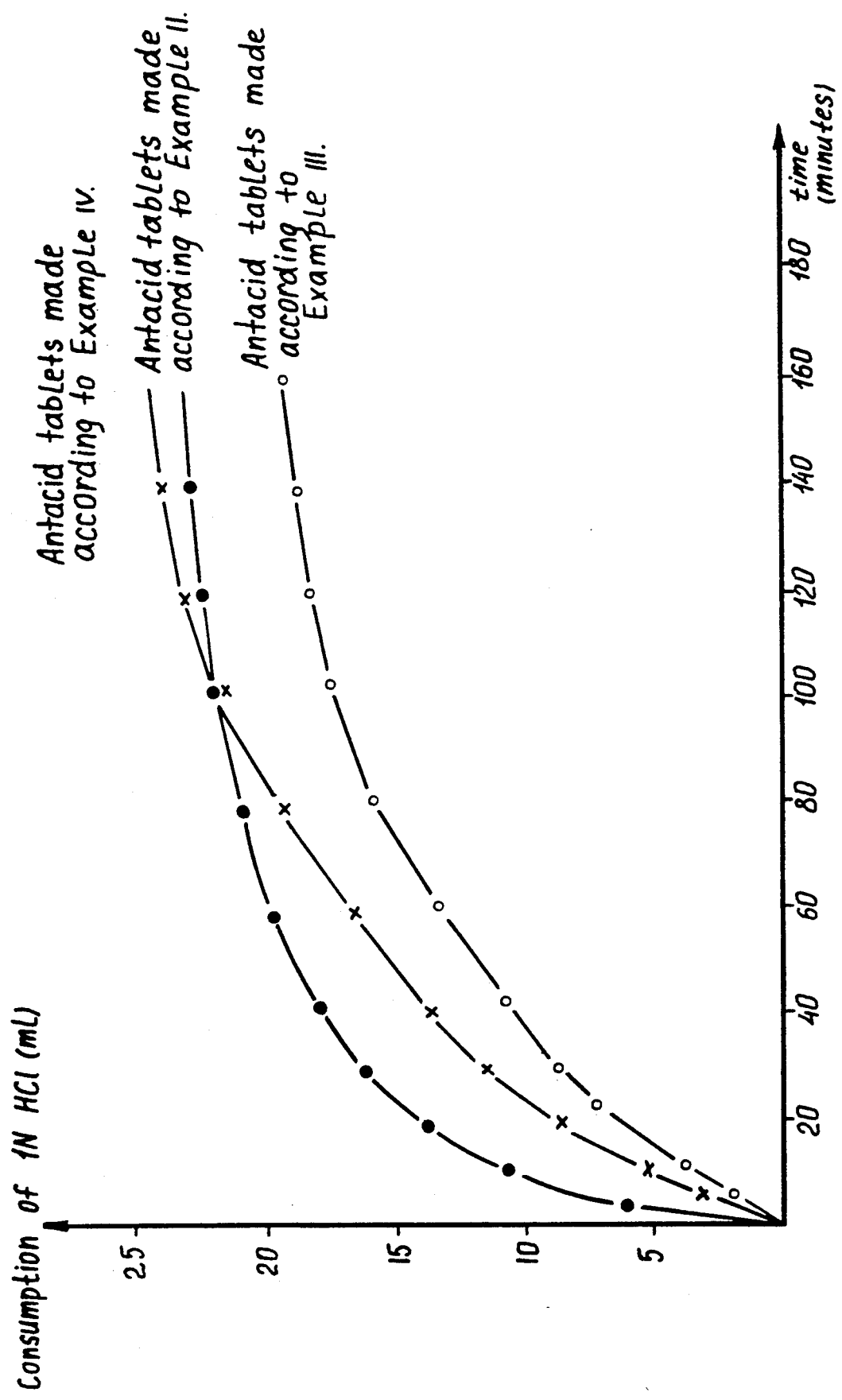
FIG. 4 is a graph of neutralization curves of the preparation of Examples I to IV.

The acid binding capacity of the tablets prepared as described in Example I to IV is equal to 17.5–25 meq of hydrochloric acid in a medium of pH 3.0 of 37° C. temperature, stirred at 300 rpm. with a magnetic stirrer: these tablets reach the degree of neutralization in 90–160 minutes. The curves of neutralization of the preparations obtained according to the Examples I to IV produced by the described method are presented in FIG. 4.

EXAMPLE V 0.05% of sodium benzoate is added to the dispersion obtained as described in Example IV. The preserved suspension so prepared may be used as a liquid pharmaceutical preparation directly or diluted with water, or it can be used as a component of other preparations produced for physiologically advantageous purposes.

EXAMPLE VI 2.5 l of deionized water are added to a mixture of 90 g of magnesium oxide and 950 g of cellulose-glycolic acid (carboxy-methyl-cellulose). The mixture is allowed to stand for 2 hours and it is then granulated using a sieve of openings of 2 mm. The granules are dryed at a temperature not exceeding 60° C. and regranulated using a sieve of openings of 1.2 mm.

The granulated product so obtained has an extraordinary swelling capacity. The dry mass is swelling in water and its volume increases about 30 times. The product is suitable for the production of "liquid wafer" tablets and it may be used also as a "bulk" laxative: that means, due to its great water retaining capacity it is suitable to produce an active laxative preparation.

We claim:

1. A pharmaceutical preparation of high acid neutralizing capacity, of increased bioavailability, and of delayed action, which comprises:
   (a) 100 parts by weight of a powdered basic magnesium compound or a powdered mixture comprising a basic magnesium compound and a basic aluminum compound; and
   (b) 2 to 2500 parts by weight of a therapeutically acceptable, water-swellable, dry or water-swollen polymeric organic acid selected from the group consisting of carboxymethyl cellulose, polyacrylic acid, polymethacrylic acid, and polyacrylic-methacrylic acid.

2. The pharmaceutical preparation defined in claim 1 in the form of a dry tablet.

3. A pharmaceutical preparation having both a delayed acid neutralizing effect and a bulk laxative effect which comprises:
   (a) a powdered, basic magnesium compound or a powdered mixture comprising a basic magnesium compound and a basic aluminum compound; and
   (b) a therapeutically acceptable, water-swellable, dry or water-swollen polymeric organic acid selected from the group consisting of carboxymethyl cellulose, polyacrylic acid, polymethacrylic acid and polyacrylic-methacrylic acid wherein the water-swellable, dry or water-swollen polymeric organic acid is present in excess of the powdered, basic magnesium compound or the powdered mixture comprising the basic magnesium compound and the basic aluminum compound.

4. The pharmaceutical preparation having both a delayed acid neutralizing effect and a bulk laxative effect defined in claim 3 wherein the polymeric organic acid is carboxymethyl cellulose, the basic magnesium compound is magnesium oxide, and wherein 950 parts of the carboxymethyl cellulose are present per 90 parts of magnesium oxide by weight.

* * * * *